United States Patent
Gaube et al.

(10) Patent No.: US 6,344,593 B1
(45) Date of Patent: *Feb. 5, 2002

(54) CONTINUOUS PREPARATION OF CYCLOHEXENE BY PARTIAL HYDROGENATION OF BENZENE

(75) Inventors: Johann Gaube, Rossdorf; Frank Doebert, Köln, both of (DE)

(73) Assignee: BASF Aktiengesellschaft, Ludwigshafen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/498,845

(22) Filed: Jul. 6, 1995

(51) Int. Cl.$^7$ .............................. C07C 5/11; C07C 13/20
(52) U.S. Cl. ..................... 585/273; 585/269; 585/271
(58) Field of Search ................... 585/273, 271, 585/269

(56) References Cited

U.S. PATENT DOCUMENTS

| | | | |
|---|---|---|---|
| 4,678,861 A | 7/1987 | Mitsui et al. | 585/266 |
| 5,424,264 A | * 6/1995 | Richard et al. | 502/261 |

FOREIGN PATENT DOCUMENTS

| | | |
|---|---|---|
| DE | 42 03 220 | 2/1992 |
| EP | 055 495 | 6/1984 |
| EP | 220 525 | 5/1987 |
| EP | 552 809 | 7/1993 |
| EP | 554 765 | 8/1993 |
| WO | 93/16971 | 9/1993 |
| WO | 93/16972 | 9/1993 |

* cited by examiner

*Primary Examiner*—Bekir L. Yildirim
(74) *Attorney, Agent, or Firm*—Keil & Weinkauf

(57) ABSTRACT

Cyclohexene is prepared by partial hydrogenation of benzene with hydrogen in the presence of water and ruthenium catalyst at elevated temperature and superatmospheric pressure by a continuous process in which benzene is introduced in gaseous form and the resulting cyclohexene is discharged in gaseous form and the catalyst is present in solution or suspension in a liquid, aqueous phase.

3 Claims, 1 Drawing Sheet

☐   Examples Ia to Ic (continuous stirred kettle; differential selectivity)

·······   Examples Ia to Ic (integral selectivity)

○   Examples 42 to 44 from U.S. Patent 4, 678, 861 (integral selectivity)

△   Examples 3a to 3e (stirred kettle cascade)

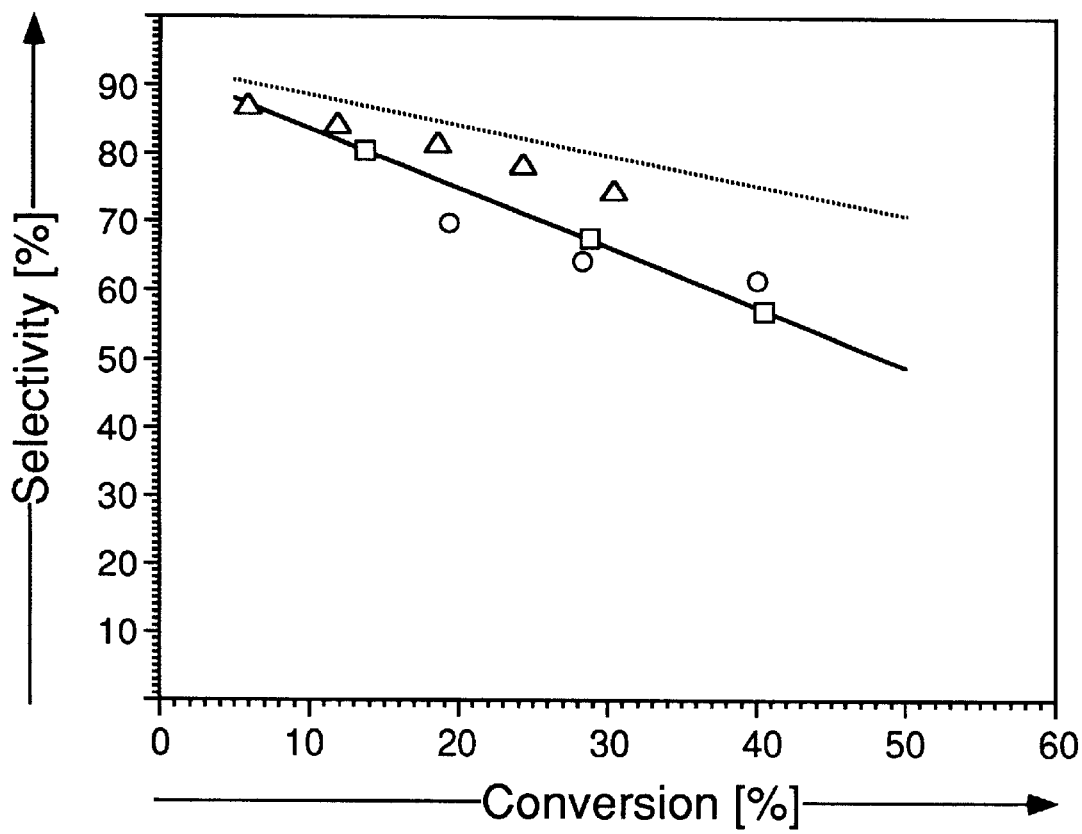
☐ Examples Ia to Ic (continuous stirred kettle; differential selectivity)
┄┄ Examples Ia to Ic (integral selectivity)
○ Examples 42 to 44 from U.S. Patent 4, 678, 861 (integral selectivity)
△ Examples 3a to 3e (stirred kettle cascade)

CONTINUOUS PREPARATION OF CYCLOHEXENE BY PARTIAL HYDROGENATION OF BENZENE

BACKGROUND OF THE INVENTION

1. Field of the Invention

The present invention relates to an improved process for the continuous preparation of cyclohexene by partial hydrogenation of benzene with hydrogen in the presence of water and a ruthenium catalyst at elevated temperatures and superatmospheric pressure.

2. Description of Related Art

U.S. Pat. No. 4,678,861 describes the batchwise partial hydrogenation of benzene to cyclohexene in a suspension, the reaction being carried out in a two-phase, liquid mixture. The disadvantage of this procedure is the separation of the catalyst from the organic phase and possibly the discharge of salts.

EP-A 552 809 describes the partial hydrogenation of benzene to cyclohexene in a system consisting of an aqueous phase, containing the catalyst suspended therein, an oily phase, containing the hydrocarbon to be hydrogenated, and a gaseous phase comprising hydrogen. One of the disadvantages of this procedure is the fact that the reaction has to be interrupted in order to separate the organic phase from the aqueous phase.

EP-B 55 495 describes the partial hydrogenation of benzene to cyclohexene in the gas phase, the maximum cyclohexene yield achieved being only 8.4%.

It is an object of the present invention to provide an improved process for the continuous preparation of cyclohexene by partial hydrogenation of benzene with hydrogen in the presence of water and a ruthenium catalyst at elevated temperatures and superatmospheric pheric pressure, which does not have the abovementioned disadvantages.

SUMMARY OF THE INVENTION

We have found that this object is achieved by a process for the continuous preparation of cyclohexene by partial hydrogenation of benzene with hydrogen in the presence of water and a ruthenium catalyst at elevated temperatures and superatmospheric pressure, wherein benzene is introduced in gaseous form and the resulting cyclohexene is discharged in gaseous form, the catalyst being present in solution or suspension in a liquid, aqueous phase.

DESCRIPTION OF PREFERRED EMBODIMENTS

According to the invention, benzene and hydrogen, together or separately, are introduced in gaseous form and the resulting cyclohexene is discharged in gaseous form. Advantageously, benzene is introduced into the reaction space together with an inert gas as a carrier, the inert gas, such as nitrogen, helium or argon, preferably being passed through a benzene-containing saturation apparatus, benzene being absorbed in gaseous form. Usually, the loading of the inert gas stream is effected at from 20 to 250° C., preferably from 50 to 170° C., the inert gas preferably being heated for this purpose upstream of the saturation apparatus. The pressure downstream of the saturation apparatus is advantageously chosen so that it corresponds to the total pressure in the reaction space.

When an inert gas is us d as a carrier gas for benzene, the benzene concentration is usually chosen to be from 0.1 to 99.9, preferably from 0.5 to 95, % by volume.

According to the invention, the gaseous benzene, with or without the carrier gas, is fed to the hydrogenation catalyst, which is present in dissolved or suspended form in a liquid, aqueous phase. The benzene partial pressure and the reaction space is generally chosen to be from 10 kPa to 1 MPa, preferably from 150 kPa to 0.5 MPa.

Observations to date have shown that the gaseous benzene can be fed into the reaction space by various methods, for example with or without a nozzle, via a simple inlet tube, into the liquid, aqueous phase or above the liquid surface.

The hydrogen partial pressure in the reaction space is chosen, as a rule, to be from 50 kPa to 5 MPa, preferably from 0.5 MPa to 4 MPa.

The reaction is advantageously carried out at from 20 to 300° C., preferably from 100 to 200° C.

The pressure and temperature conditions are advantageously co-ordinated with one another to ensure that a liquid, aqueous phase 35 is maintained and that the amount of benzene introduced corresponds to the amount of organic material discharged, consisting essentially of cyclohezene, cyclohexane and unconverted benzene. In a preferred embodiment, the pressure in the reaction space is controlled by means of an inert gas, such as nitrogen, argon or helium, preferably nitrogen, the total pressure in the reaction space being chosen to be from 0.1 to 20, preferably from 1 to 10, MPa.

The liquid, aqueous phase is advantageously agitated, preferably by stirring, the stirring speeds being chosen to be from 300 to 1500, preferably from 750 to 1500, revolutions per minute.

Observations to date have shown that all known ruthenium-containing homogeneous or suspension catalysts (supported catalysts or precipitated catalysts) may be used as catalysts. Such catalysts are described, for example, in U.S. Pat. No. 4,678,861, EP-A 220,525, WO 93/16971, WO 93116972 and EP-A 554,765, catalysts prepared according to Example 1 from U.S. Pat. No. 4,678,861 (ruthenium on a lanthanum oxide carrier) and Example 1 from EP-A 220,525 (ruthenium/zinc precipitated catalysts) and according to Example 1 from DE-A 4,203,220 (ruthenium/nickel precipitated catalysts) being particularly preferred.

A catalyst which contains from 0.01 to 100, preferably from 0.1 to 80, % by weight, based on benzene used, of ruthenium is advantageously employed.

According to the invention, the reaction is carried out in the presence of water. The weight ratio of water to catalyst is preferably chosen to be from 5:1 to 1000:1, particularly preferably from 50:1 to 500:1.

In general, water is introduced into the reaction space at the rate at which water is discharged in gaseous form, and the water may be introduced in liquid form by means of pumps or in gaseous form, for example via a saturation apparatus.

Benzene and, if desired, inert gas are advantageously added in amounts such that the catalyst is always present completely in the aqueous phase.

The reaction may be carried out in the alkaline, neutral or acidic range, depending on the catalyst system.

When the reaction is carried out in an alkaline medium, as a rule hydroxides of alkali metals or alkaline earth metals, particularly preferably sodium hydroxide or potassium hydroxide, in an amount of from 0.01 to 10, preferably from 0.1 to 5, mol/l, are added to the aqueous phase.

When the reaction is carried out in an acidic medium, as a rule acidic salts of transition metals or inorganic or organic acids, in an amount of from 0.001 to 10, preferably from 0.1 to 5, mol/l are added to the aqueous phase.

The aqueous phase advantageously contains one or more dissolved cations of transition metals of Groups 2 to 8 of the Periodic Table, such as chromium, manganese, iron, cobalt, copper or zinc, and ammonium in the form of their chlorides, nitrates, acetates, phosphates or sulfates. The amount of metal malt is advantageously from 0.01% by weight to the saturation concentration, based on the aqueous phase.

It may furthermore be advantageous to add at least one of the metal oxides selected from the group consisting of alumina, silica, zirconium dioxide, titanium dioxide, hafnium dioxide, chromium trioxide and zinc oxide to the reaction mixture. The amount of metal oxide added is preferably from 0.001 to 1% by weight, based on the amount of water used.

The discharged gas mixture, which contains essentially cyclohexene, cyclohexane, unconverted benzene and hydrogen and may contain inert gas, is generally worked up by distillation, for example by separating the organic phase by condensation from the rest of the mixture and then obtaining cyclohexene therefrom by extractive distillation.

In a preferred embodiment, a conventional stirred kettle is used for carrying out the reaction. By connecting a plurality of stirred kettles in series, flow tube behavior can be achieved. Observations to date have shown that other reactor types, such as bubble column reactors, may also be used.

The cyclohexene obtainable by the novel process is suitable for the preparation of cyclohexanol, an important starting material for the production of fiber intermediates.

The advantages of the present process are that the catalyst and salts present cannot be discharged, the salt concentration can be kept constant and the cyclohexene selectivities achieved are higher than in the past.

BRIEF DESCRIPTION OF THE DRAWING

The FIGURE sets out in graphic form the results from the experiments of the examples and from the prior art process.

EXAMPLES

Example 1

In a stirred kettle reactor (650 ml volume, completely lined with Teflon), 5 g of a ruthenium/lanthanum oxide catalyst (prepared 40 according to Example 1 from U.S. Pat. No. 4,678,861) together with 1 g of zinc chloride and 6.24 g of sodium hydroxide were covered with a layer of 250 ml of distilled water. After the reactor had been closed, the pressure in the reactor was brought to 5.0 MPa with nitrogen. Thereafter, the reactor was flushed for 4 hours with nitrogen (300 ml (S.T.P.)/min; ml (S.T.P.)=ml based on standard temperature and pressure (T=273 K, p=101.325 kPa)) with vigorous stirring (500 rpm) and was heated to 130° C. The catalyst was then activated with a hydrogen/nitrogen mixture (50 ml (S.T.P.)/min of hydrogen and 300 ml (S.T.P.)/min of nitrogen fed in) with vigorous stirring for twelve hours. The nitrogen stream was then passed through a benzene-filled saturator, the loading of the nitrogen stream being effected at about 65° C. The benzene-laden nitrogen stream (260 ml/min) was then combined with the hydrogen stream (90 ml/min) and fed to the reactor.

Before the first sample was taken (Example 1a), the reaction had been operated for 6 hours. Thereafter, the benzene and hydrogen partial pressures were varied according to Table 1 (Examples 1b and 1c), the reaction times being 3 hours in each case. No deactivation of the catalyst was observed over a period of 10 days.

The composition of the gaseous reacted mixture was analyzed by gas chromatography.

The results are summarized in Table 1.

TABLE 1

| Ex. 1 | Reaction time [h] (total) | p(H$_2$) [kPa] | p(Benzene) [kPa] | Conversion [%] | Selectivity [%] | Yield [%] |
|---|---|---|---|---|---|---|
| a | 6 | 1523 | 62 | 14.5 | 80.4 | 11.6 |
| b | 9 | 1202 | 44 | 29.2 | 68.7 | 20.1 |
| c | 12 | 1189 | 37 | 40.5 | 57.5 | 23.3 |

Examples 42 to 44 from U.S. Pat. No. 4,678,861 were used as comparative values. The values stated in Example 1 are differential selectivities. To be able to compare these values with the corresponding values from U.S. Pat. No. 4,678,861, the integral selectivity values of Example 1 were determined using the equation $$S_{int} = \frac{1}{U_{end}} \int_0^U s_{diff}(U) dU$$

where $S_{int}$ is the integral selectivity, $s_{diff}$ is the differential selectivity and $U_{end}$ is the conversion at the end of the reaction.

FIG. 1 shows the experimental results,

○ representing the results from Examples 42 to 44 of U.S. Pat. No. 4,678,861,

□ representing the experimental results from Examples 1a to 1c and

. . . representing the integral selectivities calculated for □.

Example 2

Example 1 was repeated with the following changes, under otherwise identical conditions: 10.0 g of catalyst, 2.0 g of zinc chloride and 6.32 g of sodium hydroxide.

The results are summarized in Table 2.

TABLE 2

| Ex. 2 | Reaction time [h] | p(H$_2$) [kPa] | p(Benzene) [kPa] | Conversion [%] | Selectivity [%] | Yield [%] |
|---|---|---|---|---|---|---|
| a | 12 | 764 | 86 | 14.9 | 81.9 | 12.2 |
| b | 18 | 757 | 77 | 33.3 | 67.0 | 22.3 |
| c | 24 | 743 | 57 | 40.5 | 60.8 | 24.6 |
| d | 30 | 732 | 51 | 41.1 | 61.3 | 25.2 |
| e | 36 | 786 | 35 | 44.3 | 59.1 | 26.2 |

Example 3
(Stirred Kettle Cascade)

In order to simulate a stirred kettle cascade, the following catalyst system was initially taken in the stirred kettle reactor from Example 1:

5.0 g of ruthenium/lanthanum oxide catalyst (as in Example 1), 1.2 g of ZnCl$_2$, 6.34 g of NaOH and 250 ml of distilled water. The activation of the catalyst was carried out according to the preceding examples. Thereafter, a nitrogen stream (350 ml (S.T.P.)/min) which was laden at 105° C. with benzene was fed together with hydrogen (75 ml (S.T.P.)/min) to the reactor. The composition of the hydrocarbons in the product stream was analyzed by means of a gas chromatograph. A hydrocarbon mixture which had the composition of the product gas stream from the first reaction was then fed to the reactor in order to simulate the second cascade reactor.

Three further reactions were carried out similarly to this procedure, so that a stirred kettle cascade consisting of five stirred kettles was simulated.

The reaction times were 6 hours in each case.

The results are summarized in Table 3 and shown graphically in FIG. 1 (Δ).

TABLE 3

| Reactor No. | $P(H_2)$ [kPa] | $P(C_6H_6)$ [kPa] | $P(C_6H_{10})$ [kPa] | $P(C_6H_{12})$ [kPa] | Conversion [%] | Selectivity [%] | Yield [%] |
|---|---|---|---|---|---|---|---|
| 1 | 786 | 158 | 9.0 | 1.3 | 6.1 | 87.4 | 5.3 |
| 2 | 785 | 147 | 16.6 | 3.0 | 11.8 | 84.7 | 10.0 |
| 3 | 785 | 135 | 24.4 | 5.6 | 18.2 | 81.3 | 14.8 |
| 4 | 785 | 124 | 30.5 | 8.6 | 24.0 | 78.0 | 18.7 |
| 5 | 786 | 112 | 35.8 | 12.7 | 30.1 | 73.8 | 22.1 |

We claim:

1. The process for the continuous preparation of cyclohexene by partial hydrogenation of benzene with hydrogen in the presence of water, an alkaline agent, a zinc compound and a ruthenium catalyst at elevated temperatures and superatmospheric pressure, wherein benzene is introduced in gaseous form and the resulting cyclohexene is discharged in gaseous form, the catalyst being present in solution or suspension in a liquid, aqueous phase and the reaction is carried out at a weight ratio of water to catalyst of from 5:1 to 1000:1.

2. The process as defined in claim 1, wherein the reaction is carried out at a hydrogen partial pressure of from 50 kPa to 5 MPa.

3. The process as defined in claim 1, wherein the reaction is carried out at a benzene partial pressure of from 10 kPa to 1 MPa.

* * * * *